United States Patent [19]

Suzuki et al.

[11] Patent Number: 5,215,744
[45] Date of Patent: * Jun. 1, 1993

[54] METHODS FOR THE TREATMENT OF TUMORS

[75] Inventors: Nobuo Suzuki, Funabashi; Yoshiaki Takakubo, Mishima, both of Japan

[73] Assignee: Boehringer Ingelheim GmbH, Fed. Rep. of Germany

[*] Notice: The portion of the term of this patent subsequent to Mar. 5, 2008 has been disclaimed.

[21] Appl. No.: 546,305

[22] Filed: Jul. 2, 1990

Related U.S. Application Data

[63] Continuation-in-part of Ser. No. 207,622, Jun. 16, 1988, Pat. No. 4,997,645.

[30] Foreign Application Priority Data

Jun. 16, 1987 [EP] European Pat. Off. ...... 87/108708.6

[51] Int. Cl.$^5$ ............................................. A61K 37/66
[52] U.S. Cl. .................. 424/85.4; 424/85.5; 424/85.6; 424/85.7; 530/351
[58] Field of Search ............ 424/85.5, 85.6, 85.7, 424/85.4

[56] References Cited

U.S. PATENT DOCUMENTS 3,031,450  4/1962  Fischer et al. ............... 260/247.5
4,997,645  3/1991  Suzuki et al. ................. 424/855

FOREIGN PATENT DOCUMENTS 0084953  1/1983  European Pat. Off. .

OTHER PUBLICATIONS

Ambrus et al., *Proc. Amer. Assoc. Canc. Res.* 23:189 (1982).
Bastida et al., *Cancer Res.* 45:4048–4052 (1985).
Biddle et al., *Proc. Soc. Exp. Biol. Med.* 177:487–490 (1984).
Chan et al., *Cancer Res.* 45:3598–3604 (1985).
Chan et al., *Cancer Treat. Reports* 69:425–430 (1985).
Chervinsky et al., *Proc. Amer. Assoc. Canc. Res.* 24:309 (1983).
European Search Report for the corresponding European patent application.
Galabov et al., *Acta Virol.* 26:137–174 (1982).
Goldstein et al., *Cancer Res.* 46:4315–4329 (1986).
Grem et al., *Chem. Abst.* 103:30 (1985).
Grem et al., *Cancer Res.* 45(7):2967–2972 (1985).
Nelson et al., *Cancer Res.* 44:2493–2496 (1984).
Slichter, S. J. et al., *Blood* 59(6):1252-8 (Jun. 1983).
Weber, *Cancer Res.* 43:3466–3492 (1983).
Wolf et al., *J. Med.* 15:15–21 (1984).
Zhen et al., *Cancer Res.* 43:1616–1619 (1983).

Primary Examiner—David L. Lacey
Assistant Examiner—Shelly J. Guest
Attorney, Agent, or Firm—Sterne, Kessler, Goldstein & Fox

[57] ABSTRACT

Disclosed is a method of treating tumors capable of being treated with interferon by administering interferon and dipyridamole, or pharmaceutically acceptable salts thereof, in amounts sufficient to enhance the antitumor effect of interferon. Further disclosed is a pharmaceutical composition comprising interferon and dipyridamole.

17 Claims, 18 Drawing Sheets

METHODS FOR THE TREATMENT OF TUMORS

This application is a continuation-in-part application of U.S. application No. 07/207,622 filed Jun. 6, 1988, now U.S. Pat. No. 4,997,645 which is incorporated herein in its entirety.

BACKGROUND OF THE INVENTION

1. Field of the Invention

The present invention relates generally to the treatment of tumors, in particular the treatment of tumors using an interferon. More specifically, the invention relates to the use of dipyridamole for enhancing the tumor-growth inhibitory action of an interferon, a method of treating a patient suffering from a tumor by combined therapy with dipyridamole and an interferon, the use of dipyridamole and interferon for preparing such pharmaceutical preparations for treating tumors, and to pharmaceutical preparations so produced.

2. Brief Description of the Background Art

Information on the inhibitory action of human interferon (HuIFN) on the growth of cultured cell lines has been accepted as viable for clinical trials of HuIFN as antitumor therapy (*Adv. Cancer Res.*, Vol. 46, Academic Press, London (1986), and Stewart, *The Interferon System*, Springer-Verlag, Wien/New York, (1981).

Recently, it has been found that the susceptibility of human cells to the anticellular effects of HuIFN correlated with radio-sensitivity and/or DNA-repair capacity. Suzuki et al., *Virology*, 135:2029, (1984); *Mutation Res.*, 106:357-376, (1982); *J. Gen. Virol.*, 67:651-661 (1986), Yarosh et al., *Carcinogenesis* 6:883-886 (1985) *Biophys. Res. Commun.*, 72:732 (1976)). It has also been found that the cellular response mechanisms for DNA damage are modified by HuIFN treatment itself; for example, the increase of DNA-repair synthesis levels and enhancement of survival of cells treatment with agents which can cause structural damage of DNA. Suzuki et al., *Virology*, 135:20-29, (1984); *Mutation Res.*, 175: 189-193 (1986)). Therefore, it seems undesirable to carry out antitumor therapy by HuIFN in combination with other anti-cancer agents which damage DNA because of HuIFN-induced resistance to the agents, and there is a need for an agent which does not itself cause DNA damage but can enhance the antitumor activity of interferon.

The compound 2,6-bis(diethanolamine)-4,8-dipiperidino-pyrimido[5,4-d]pyrimidin, which has the generic name dipyridamole, and its preparation have been described in U.S. Pat. No. 3,031,450.

Dipyridamole is a well known vasodilator and also has platelet aggregation inhibiting properties. In view of these properties, it has found widespread use for many years in the treatment of chronic coronary insufficiency and in the prophylaxis and treatment of heart infarcts as well as in the prophylaxis of arterial thrombosis.

More recently, the possible use of dipyridamole in tumor therapy has been investigated. This interest has derived from the observation that while it does not damage DNA, dipyridamole is an effective blocker of the salvage pathway of DNA synthesis, and that it can inhibit nucleoside transport through the cell membrane and so block restoration of internal cellular nucleoside levels, thus potentially inhibiting important steps in tumor cell synthesis. *Biochem. Biophys. Acta*, 58:435-447, (1968), and *Biochem. Biophys. Acta*, 211:88-94, (1970).

In view of this property, the effects of dipyridamole, both alone and in combination with various anti-cancer agents, have been investigated. Thus, Chan et al., *Cancer Treat. Rep.*, 69:425-430, (1985) found that dipyridamole can potentiate the activity of N-phosphoracetyl-L-aspartate (PALA) in vitro and in vivo PALA is a pyrimidine anti-metabolite which is thought to inhibit an early step in de novo pyrimidine synthesis, causing depletion of intracellular pyrimidine nucleotides. In another study Chan et al., *Cancer Research*, 45:3598-3604 (1985) reported that dipyridamole increased PALA activity against a human ovarian carcinoma cell line while exhibiting no cytotoxicity of its own.

Zhen et al., *Cancer Research*, 43:1616-1619, (1983), reported that the addition of a combination of cytidine, deoxycytidine and guanosine at an optimal concentration of 8 $\mu$M each protected rat hepatoma 3924 A cells from the growth-inhibitory action of the antiglutamine drug Acivin, and that this protection was blocked by dipyridamole at a concentration of 6 $\mu$M.

Nelson et al., *Cancer Research* 44: 2493-2496, (1984) reported that dipyridamole enhanced the toxicity of methotrexate (MTX) towards chinese hamster ovary cells both in vitro and in vivo; however, the antitumor activity of MTX towards certain other tumors, namely ridgway osteogenic sarcoma and LIZIO leukemia was not dramatically improved.

Various other publications describe the testing of dipyridamole together with anti-cancer agents against tumor cells, e.g. with cytarabine (*Cancer Treat. Rep.* 68: 361-366, (1984) and 2'-deoxyadenosine (*Cancer Research* 45: 6418-6424, (1985).

In addition, some investigations have been carried out on the use of dipyridamole alone as an anti-cancer drug. Thus, in the investigation on the combined action of dipyridamole/acivin, Weber, *Cancer Research*, 73: 3466-3492, (1983), also showed that dipyridamole was effective in killing Hepatoma 3924A cells. Bastida, *Cancer Research* 45: 4048-4052, (1985), reported a potential metastatic effect of dipyridamole, possibly resulting from inhibition of tumor cell metabolism or suppression of one or more of the mechanisms involved in the ability of tumor cells to activate platelets.

Work has also been carried out on the structurally related compound 2,6-bis-(diethanolamino)-4-piperidino-pyrimido[5,4-d]pyrimidine (Mopidamole) as an anti-cancer drug.

Gastpar, Laryng, Rhinol., Otpl. 62: 578-525 (1983) reported that mopidamole potentiates the antimitotic effect of interferon and its natural killer cell activating activity. He reports in the same article that "the adding of mopidamole to a culture of a human promyelocytic leukemic cell line promotes a reverse transformation of the malignant cells to normal which appears to be a permanent phenotypic change. Furthermore, mopidamole was shown to diminish significantly spontaneous lung metastases in syngeneic Wilms Tumor (nephroblastoma) of the rat, the C1300 neuroblastoma of the mouse and the HM-Kim mammary carcinoma of the rat."

The use of mopidamole in the above investigation was based on its ability to increase cAMP levels, resulting in an inhibition of 3H-thymidine incorporation into neoplastic cells and a direct inhibition of the mitotic rate. The effect on cAMP levels derives from mopidamole's inhibition of PDE induced decomposition of cAMP, it may also stimulate the synthase and/or release of prostacyclin from the vessel wall which in turn activates adenylate cyclase involved in cAMP synthesis. Dipyridamole is, however, known to be much weaker PDE inhibitor than mopidamole.

It must also be observed that the teaching in the literature of the combination of mopidamole with interferon is confusing. Ambrus, J. L. et al. *Proc. Am. Assoc. Cancer Res.* 23: 183 (1932) state that mopidamole potentiates the antitumor effect of leukocyte and fibroblastic interferon in tissue culture, and in *Proc. Soc. Exp. Biol. Med.* 177: 487-490 (1984) state that mopidamole potentiates the growth inhibitory effect of human fibroblastic β-interferon. Wolf et al., *J. Med.* 15: 15-21 (1984) concludes that, in contrast to its effect with human fibroblast interferon, no synergistic inhibitory effect between mopidamole and a variety of α and γ interferon could be observed. Finally, Ambrus et al. *Proc. Am. Assoc. Cancer Res.* 24: 309 (1983) state that, in contrast to some previous reports, no synergism was seen between interferon and mopidamole.

Galabov et al. *Acta. Virol.* 26 (3): 137-174 (1982) described a further investigation with dipyridamole. European Patent Application 0.084.953. Galabov et al. reported that dipyridamole induced interferon production in vitro in explanted mouse peritoneal leukocytes and other cells and it induced interferon in mice after I.V. administration. However, this work has not been confirmed by other groups.

It is no where taught or suggested in the literature either to mole in combination with an interferon in antitumor therapy, or suggested that any worthwhile results could be expected from such a combined therapy.

Figure 1:
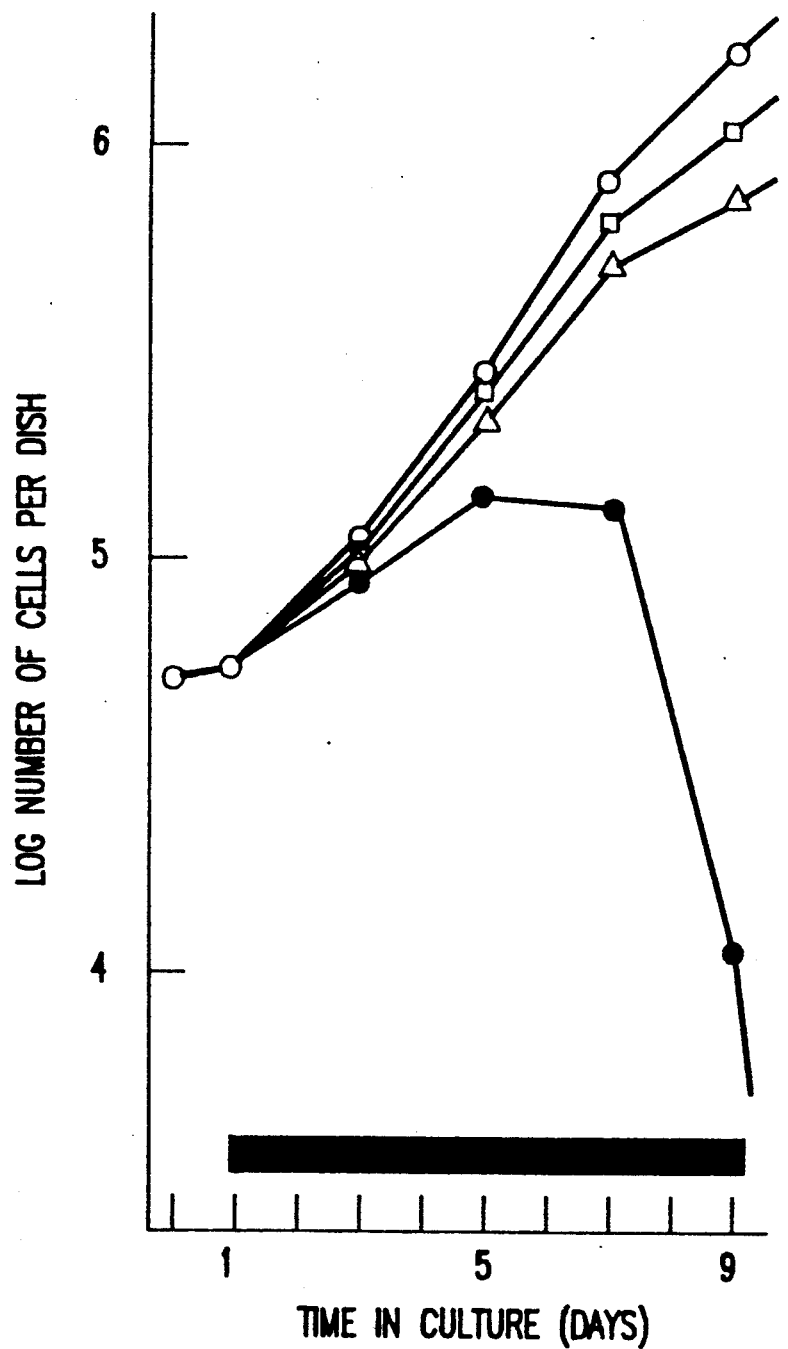
FIG. 1
Figure 2A:
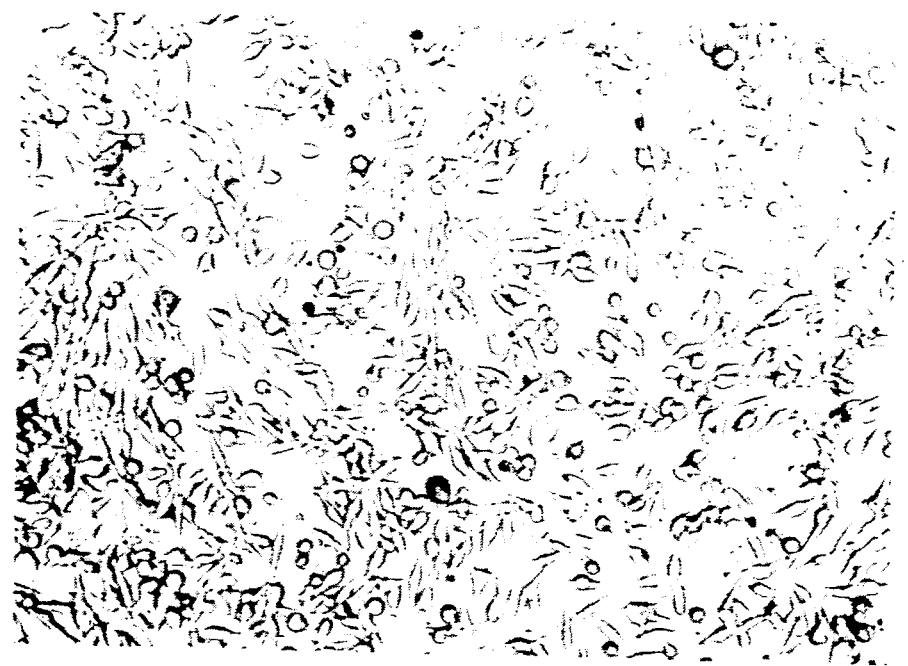
Figure 2B:
Figure 2C:
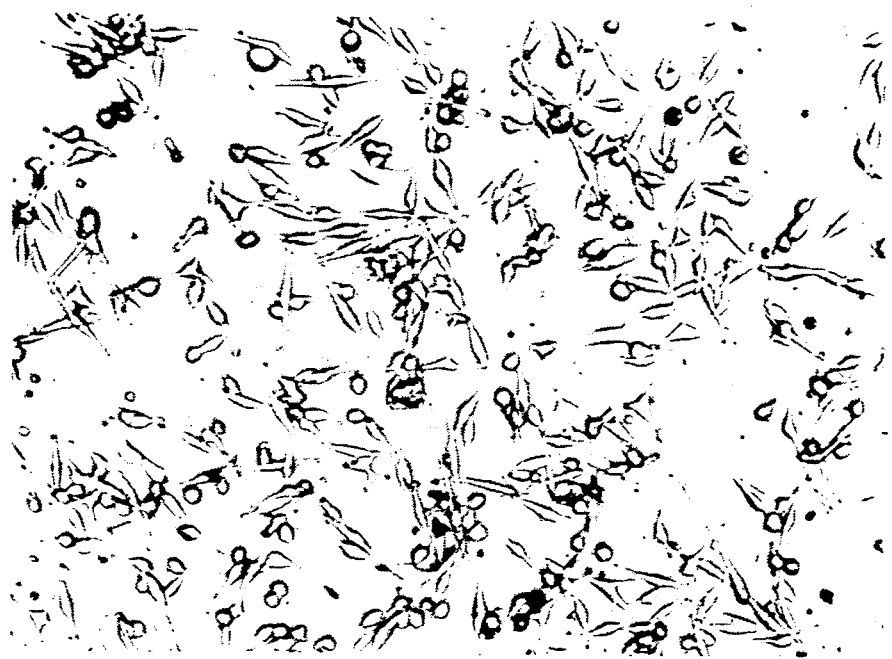
Figure 2D:

Growth curves of MM-1CB. o, treatment with mock HuIFN-β corresponding to 10 units/ml HuIFN-β: □, treatment with 0.1 μM dipyridamole; Δ, treatment with 10 units/ml HuIFN-β; ▲, treatment with 10 units/ml HuIFN-β and 0.1 μM dipyridamole; ■, period of treatment with drugs.

FIG. 2

Morphology and cell distribution 6 days after continuous exposure to HuIFN-β and dipyridamole in MM-1CB. (A) mock HuIFN-β corresponding to 10 units/ml HuIFN-β, (B) 0.1 μM dipyridamole, (C) 10 units/ml HuIFN-β, (D) 10 units/ml HuIFN-β and 0.1 μM dipyridamole.

FIG. 3

(A) Cell survival percents 6 days after continuous exposure to 0.1 μM dipyridamole and various units of HuIFNα (Δ and ▲), ), -β (o and ●) and -γ (□ and ■) and in MM-1CB. Δ, o, and □, treatment with HuIFN alone; ▲, ● and ■, treatment with HuIFN and dipyridamole.

(B) Cell survival percents 6 days after continuous exposure to units/ml HuIFN-α (▲), -β (●) and -γ (■) in combination with various concentrations of dipyridamole in MM-1CB. o, treatment with dipyridamole alone.

FIG. 4

(A) Cell survival percents 4 days after continuous exposure to 0.1 μM and various units of HuIFN-α in KT cells. o, treatment with HuIFN-α alone; ●, treatment with Hu IFN-α and dipyridamole.

(B) Cell survival percents 4 days after continuous exposure to 10 units/ml HuIFN-α and various concentrations of dipyridamole. o, treatment with dipyridamole alone; ●, treatment with HuIFN-α and dipyridamole.

FIG. 5

(A) cell survival percents 6 days after continuous exposure to 0.1 μM and various units of HuIFN-β in PLC/PRF/5 cells. o, treatment with HuIFN-β alone; ●, treatment with HuIFN-β and dipyridamole.

(B) Cell survival percents 6 days after continuous exposure to 10 units/ml HuIFN-β and various concentrations of dipyridamole. o, treatment with dipyridamole alone; ●, treatment with HuIFN-β and dipyridamole.

FIG. 6

Morphology and cell distribution 2 days after exposure to HuIFN-α and dipyridamole in KT cells. (A) Control, (B) 0.1 μM dipyridamole, (C) 10 units/ml HuIFN-α, (D) 10 units/ml HuIFN-α and 0.1 μM dipyridamole.

FIG. 7

Morphology and cell distribution 6 days after exposure to HuIFN-β and dipyridamole in PLC/PRF/5 cells. (A) Control, (B) 0.1 μM dipyridamole, (C) 10 units/ml HuIFN-β, (D) 10 units/ml HuIFN-β and 0.1 μM dipyridamole.

FIG. 8

DNA synthetic activity test in KT cells with [$^3$H] deoxythymidine incorporation into acid-insoluble cell materials 24 hr. after exposure to agent o IFN-o, Hu IFN-α, ● Hu IFN-α and 0.1 μM dipyridamole.

FIG. 9

Comparison of tumor size on nude mice after dipyridamole and interferon treatment. Treatment was performed as follows:

Male athymic nude mice (BALB/cA JcL-nu) used were 4 week old and weighed 14 to 18 g at the beginning of the experiment. All mice were given a basal diet (FR-II, Funabashi Nojo Co., Ltd., Funabashi) ad libitum.

MM-1CB cells ($1 \times 10^6$) were injected by syringe into the upper part of the right femur of mice. Starting 3 days after tumor implantation, mice were injected s.c. with 0.1 ml volumes of drugs (interferon α2C: $10^4$ IU and dipyridamole: 0.2 μmoles) every 2nd day for a total of 62 days. Control animals were treated with phosphate buffered saline.

On day 62 post tumor implantation the size of each tumor was measured by caliper (two dimensions) and the measurements were converted to an approximation of tumor weight employing the formula: $(a \times b^2)/2$, where a and b are the length and width of tumor, respectively. The mean of results from three mice under each treatment was depicted.

FIG. 10

Growth rate of tumors after the apparent tumor appeared and then were treated with agents.

On day 27 post MM-1CB cells injection $1 \times 10^5$ IU interferon β and 0.1 μmole Dipyridamole were injected s.c. around the tumor every 2nd day.

O control
● the two agents combination
□ injection of dipyridamole alone for 2 weeks until the 27th day and then the continuous treatment with the two agents Δ injection of dipyridamole alone for 3 weeks until the 27th day and then the continuous treatment with the two agents.

FIG. 11

Survival percents of MM-1CB cells 6 days after treatment with dipyridamole (DP) and human interferon β (IFN β).

Experimental numbers (Exp. Nos.) 1, 2, and 3 were the results obtained under reported cell-culture-conditions.

In Exp. Nos. 4 and 5, treatment with DP alone and without IFN β was done during hours of the experiment schedule, respectively.

In Exp. No. 6 IFN β treatment alone, without the DP addition, was done after DP treatment alone for the first 24 hours of the experimental schedule; after the DP treatment culture medium was depleted and cells were washed three times with Eagle's minimal essential medium, followed by being cultured with medium containing IFN β.

FIG. 12

Alkaline sucrose gradient assay in MM-1CB cells with and without dipyridamole and interferon β treatment.

Cells ($2 \times 10^5$), prelabelled with [$^{14}$C]Thymidine, were seeded in 60 mm culture dishes and then cultured with and without agents. After the indicated tie cells were scraped off from the dishes and suspended in ice-cold phosphate-buffer saline solution containing 10 mM EDTA.

The cell suspensions were then exposed to 100R of X-rays in order to facilitate the unwinding and separation of DNA strands, and the solution containing SDS was applied to the cells, 2% of the final concentration of sodium dodecil sulfate (SDS).

The cell lysates were layered on alkaline solution with 5-20% sucrose gradients containing 0.1M NaOH and 0.1M NaCl. Then the gradients were immediately centrifuged at 10,000 rpm for 17 hr at 20° C. in a Hitachi RPS55T rotor.

After centrifugation, solutions were fractionated and collected onto Whatmann 17 CHROMA paper strips. Radioactivity of acid-insoluble materials on the strips were counted in toluene based scintillator. The percentage of the total dpm in each fraction was calculated taking the input dpm as 100%.

A control
B 10 μM dipyridamole exposure for 24 hr;
C $10^3$ IU/ml IFNβ exposure for 48 hr;
D exposure to 10 μM dipyridamole alone for 24 hr and then the continuous exposure to $10^3$ IU/ml IFNβ alone for 24 hr. Arrow means that the most part DNA shifted into lower molecular mass.

FIG. 13

Protease activity after dipyridamole exposure for 30 min in MM-1CB cells. Assay methods were similar to those described elsewhere (Suzuki et al., *Mutation Res.* 198:207-214 (1988)). Results were expressed as the total amount of $^{125}$I-radioactivity released from the labelled fibrin per protein contents.

FIG. 14

Survival percents of SEKI-F melanoma cells 6 days after continuous exposure to dipyridamole and interferon β. Culture and the exposure conditions were the same as described in the previous manuscript.

O treatment with dipyridamole alone;
Δ treatment with dipyridamole and 100 IU/ml interferon β
□ treatment with dipyridamole and 500 IU/ml interferon β
● treatment with dipyridamole and 1000 IU/ml interferon β.

SUMMARY OF THE INVENTION

The present inventors have found that dipyridamole, a compound which does not have DNA damaging properties, or a pharmacologically acceptable salt thereof, unexpectedly enhances the antitumor effect of an interferon chosen from HuIFN α, β or γ.

Accordingly, a first aspect of the present invention comprises the treatment of a patient suffering from a tumor which comprises administering dipyridamole, or a salt thereof, to the patient in an amount sufficient to enhance the antitumor effect of an interferon which is also administered to the patient.

A second aspect of the invention comprises a method of treating a patient suffering from a tumor, which comprises administering an interferon and dipyridamole, or a pharmaceutically acceptable salt thereof, to said patient, the dipyridamole or salt being administered in an amount which enhances the antitumor effect of the interferon.

A further aspect of the invention comprises dipyridamole or a pharmaceutically acceptable salt thereof for the manufacture of a pharmaceutical composition suitable for enhancing the antitumor effect of an interferon when administered to a patient suffering from a tumor and to whom said interferon is also administered.

Yet a further aspect of the present invention comprises an interferon for use in manufacturing a pharmaceutical composition for use together with dipyridamole or a pharmaceutically acceptable salt thereof in the treatment of a tumor, whereby said dipyridamole or salt is used to enhance the antitumor effect of said interferon.

Another aspect of the present invention comprises a pharmaceutical composition containing an interferon and dipyridamole or a pharmaceutically acceptable salt together with conventional pharmaceutical excipients.

DESCRIPTION OF THE PREFERRED EMBODIMENTS

The term interferon, as used herein, means any of the leucocyte (α), fibroblast (β) or immune (γ) interferons.

The amino acid sequences of the various interferons, their preparation by recombinant technology and the preparation of pharmaceutical compositions containing them are described in the literature.

For example, the amino acid sequence and recombinant preparations of HuIFNα$_2$a is described in European Patent Publication No. 0.043.98; for HuIFNα$_2$b in European Patent Publication No. 0.32.134, and for HuIFNα$_2$c in European Patent Publication No. 0.115.613. Similarly, European Patent Publication No. 0.028.033 describes the amino acid sequence and production by recombinant techniques of HuIFN-β. The amino acid sequence and recombinant preparation of HuIFN-γ is described in European Patent Publication No.0.051.873.

The dipyridamole or salt thereof and interferon may be administered such that they are simultaneously present at the tumor site. In this manner, they are administered simultaneously or substantially simultaneously. The term "substantially simultaneously" means "at about the same time" with the only limitation being that both substances must be present together at the tumor site.

Alternatively, administration may be sequential. That is, dipyridamole is administered for a time sufficient for saturation of the tumor site followed by administration with interferon alone or in combination with dipyridamole. This pretreatment with dipyridamole followed by treatment with interferon, or interferon and dipyridamole, shows at least a similar synergistic antitumor effect as simultaneous administration. In fact, dipyridamole pretreatment may be more effective in treating tumors than simultaneous treatment.

The pretreatment with dipyridamole is for a period of time to saturate the tumor site. The length of time of pretreatment before the administration of interferon may vary. Generally, the pretreatment period can be as short as several hours, usually at least 24 hours, ranging to as long as several weeks, for example, about 3 to about 6 weeks.

In any given case, the coordination of the administration of the interferon and dipyridamole will be determined according to the pharmacokinetics of the compound which will be known to persons of ordinary skill in the art of the invention. It is presently considered that the preferred effective plasma level of dipyridamole for the antitumor treatment is about 0.1 $\mu M$ (50 ng/ml) and the effective plasma level of interferon for the treatment about 10 I.U./ml.

The recommended dosages for both dipyridamole and its salt and the interferons are based on the above proposed plasma levels. It will be clear that actual dosages may be altered by the attending physician depending upon the circumstances and conditions of the individual patient.

For the present invention, the interferon may be administered by the parenteral route. The dosage and dosage rates are preferably about $1 \times 10^6$ to $10 \times 10^6$ I U., preferably $1 \times 10^6$ to $3 \times 10^6$ I.U. given twice daily in the case of intravenous administration and once daily in the case of intramuscular injection.

The preparation of suitable dosage forms for human interferons is well known.

To produce a convenient dosage form for parenteral use, an appropriate amount of HuIFN may be dissolved in 5% human serum albumin, if necessary containing suitable buffer solution. This resulting solution is then passed through a bacteriological filter and the filtered solution is distributed between vials under aseptic conditions, each vial containing an appropriate amount of the interferon and, if desired, lyophilized. The glass vials are preferably stored under cool conditions ($-20°$ C.) before use. The interferons may be formulated in known manner in order to obtain pharmaceutically usable compositions, the interferon being mixed with a pharmaceutically acceptable carrier substance; conventional carriers and their formulation are described by E. W. Martin in *Remington's Pharmaceutical Sciences*, which is herein incorporated by reference.

The dipyridamole or salt thereof can be administered by any of the usual routes of administration, for example, orally or parenterally. At present, the preferred route of administration is oral. The recommended dosages are 25 to 100 mg, preferably 30 to 60 mg twice daily. However, if desired, 10 to 20 mg of dipyridamole may be used as one dose, being administered intravenously in one hour together with interferon.

Dipyridamole is commercially available under the trademark Persantin ™ in a number of forms. For instance, injection solution containing 10 mg dipyridamole and dragees containing 25 mg and 75 mg dipyridamole are described in the Rote Liste 1987 published by the Bundesverband der Pharmazeutischen Industrie e.V., D-6000 Frankfurt a.M., West Germany. Suitable dosage forms containing various amounts of dipyridamole can be prepared using standard techniques. In addition, a number of special galenic forms have been described in the literature which are aimed at providing either accelerated or delayed (sustained) release and resorption of dipyridamole, such as the retard capsule form described in European Patent Publication No. 0.032.562 and the instant release form described in European Patent Publication No. 0.068.191. A further delayed release galenic form is described in British Patent No. 2.025.227.

The present invention is predicated on the observation that in various established human cell lines, dipyridamole demonstrated the surprising property of enhancing the growth inhibition effects of various human interferons.

Studies conducted to test the observation that simultaneous administration of dipyridamole enhances the tumor growth inhibition effects of interferon are described below:

Four established cell lines were used. These were MM-1CB, derived from tissues of malignant melanoma (level IV, $pT_4N_0M_0$) in a 70-year-old man (*Jpn. J. Dermatol.* 96:947 (1986)); KT, derived from metastatic brain tumor in a 52-year-old woman (*J. Rad. Res.* 26:59 (1985) and The 44th Meeting of Japanese Cancer Association, 718 (1985)); PLC/PRF/5, derived from human hepatoma (*Brit. J. Cancer* 34:509–515 (1976)) and a transformed cell line RSa (*Virology* 135:20–29 (1984), and *J. Natl. Cancer Inst.* 56:919–926 (1976)).

Cells were cultured with Eagle's minimal essential medium (EMEM) containing 10% fetal bovine serum (GIBCO, U.S.A.) and antibiotics (100 g streptomycin/ml and 100 units penicillin G/ml), in an incubator at 37° C. under 5% $CO_2$.

Natural HuIFN preparations; $\alpha$ ($10^8$ international reference units (I.U.)/mg protein), $\beta$ ($10^7$ I.U./mg protein) and mock $\beta$, and $\gamma$ ($10^6$ I.U./mg protein), were purchased from ENZO BIOCHEM INC. (U.S.A.), Flow-Rentschler Inc. (W. Germany) and Paesel GmbH & Co. (W. Germany) Dipyridamole and Mopidamole were provided by Boehringer Ingelheim GmbH (W. Germany). Other chemical agents were purchased from the Nakarai Co., Ltd., Japan.

Cell Proliferation Inhibition Test

Logarithmically growing cells of each cell line were seeded: $1-5 \times 10^4$ cells per one 60-mm dish (IWAKI, Japan), and 20 hours after the seeding, were washed and re-fed with the medium containing HuIFN preparations and dipyridamole with or without dipyridamole. Changes of medium with and without agents were carried out every other day. The viable cells were determined by trypan-blue exclusion test and counted with a hemocytometer. The survival percentage ratio was expressed as (counts of viable cells in test dishes per counts of viable cells in control dishes) x 100%, as described elsewhere in, e.g., *Mutation Research* 106:357–376 (1982) and *J. Gen. Biol.* 67:651–661 (1986).

DNA Synthetic Activity Test

[$^3$H]dTHD uptake into acid insoluble materials were estimated in KT and RSa cells treated with the various agents, as described in *J. Gen. Virol.* 67:651–661 (1986).

Microscopic Study

Cells seeded in test dishes were observed and photographed using OLYMPUS IMT-2 (x 10031 x1500 amplification).

Most of experiments were carried out under a dim light or in the dark. Results were expressed as the mean of values obtained from more than two independent experiments.

Figure 3A:
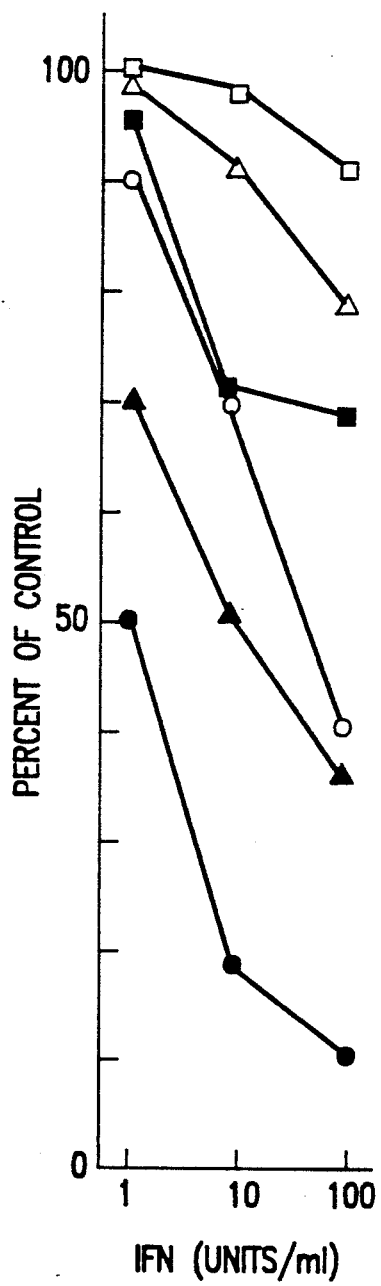

In the investigation on MM-1CB cells treatment with either agent alone, 10 units/ml HuIFN-$\beta$ or 0.1 $\mu$M dipyridamole, was only slightly effective in suppressing cell proliferation, whereas considerable inhibition of cell growth was evident upon treatment of the cells with both these agents together for more than 4 days (FIG. 1). After the combined treatment, the cells appeared morphologically impaired in comparison with cells treated with mock HuIFN-$\beta$, whereas cells treated with each agent alone did not (FIG. 2). When the cells were treated continuously with 0.1 $\mu$M dipyridamole, the additive effect with HuIFN-$\alpha$, -$\beta$ and -$\gamma$ was also observed (FIG. 3A). Higher concentrations and even lower concentrations down to 0.01 $\mu$M of dipyridamole were effective in enhancing the anticellular effect of HuIFN (FIG. 3B).

Figure 4A:
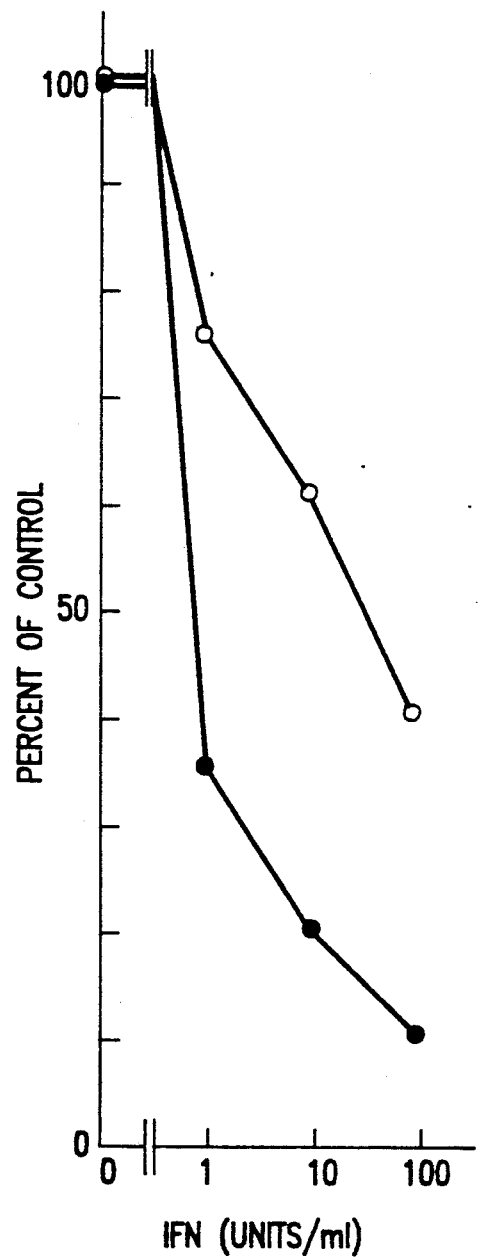
Figure 4B:
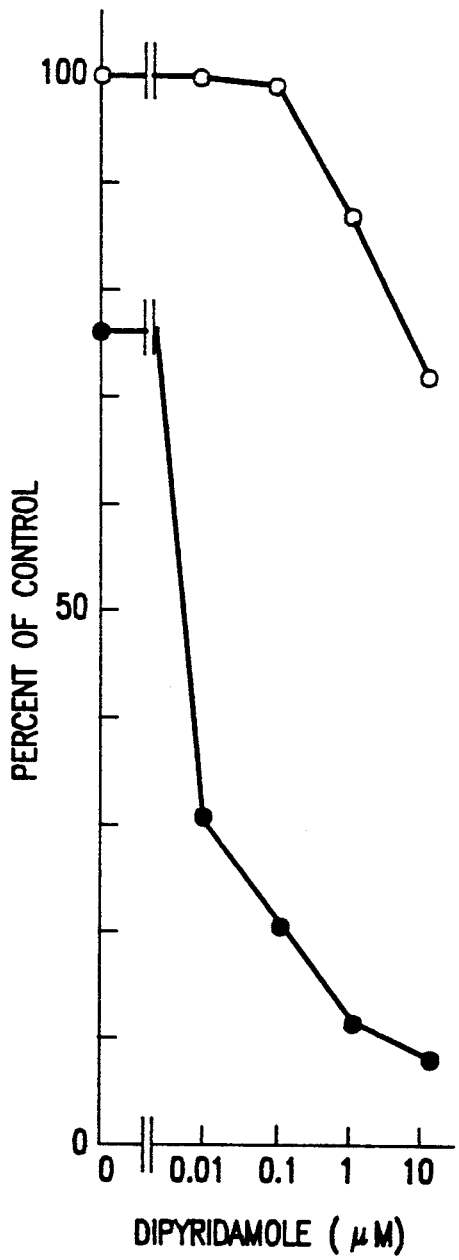
Figure 5A:
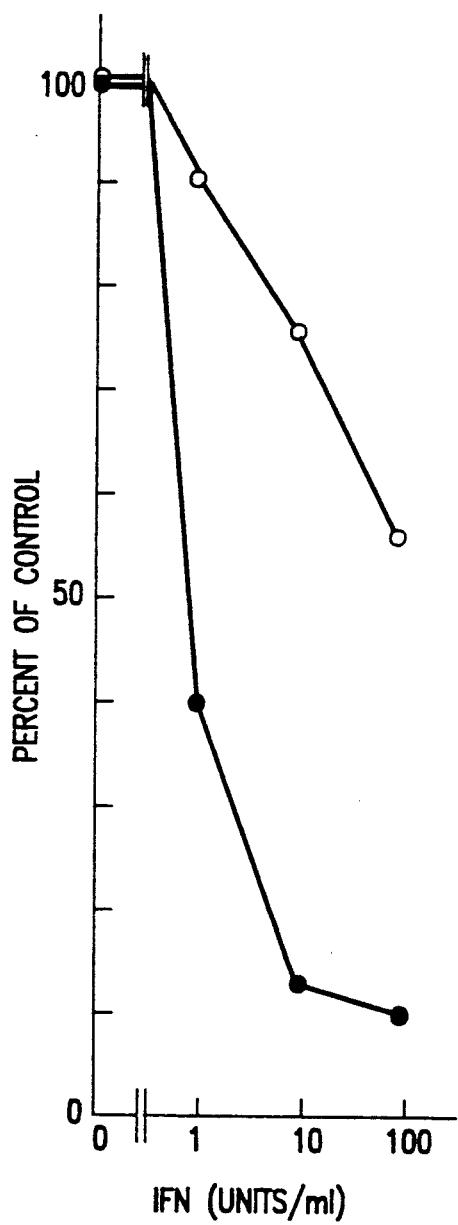

When the other two cell strains: metastatic brain tumor (KT) and hepatoma (PLC/PRF/5) cell lines, were treated with HuIFN and dipyridamole, both cells showed high susceptibility to the synergistic inhibitory activity (FIGS. 4 and 5). Although cell replication of KT cells was greatly inhibited by HuIFN-$\alpha$, the inhibition of cell replication was enhanced in comparison with the simultaneous exposure to dipyridamole (FIG. 4). Even less than 0.1 $\mu$M dipyridamole, at concentration dipyridamole alone, which scarcely influenced KT cell replication, could enhance the inhibitory effect of HuIFN-$\alpha$ (FIG. 4B). It was evident that cellular morphological conditions of both cell strains also showed impairment after the combination treatment (FIGS. 6 and 7).

Figure 3B:
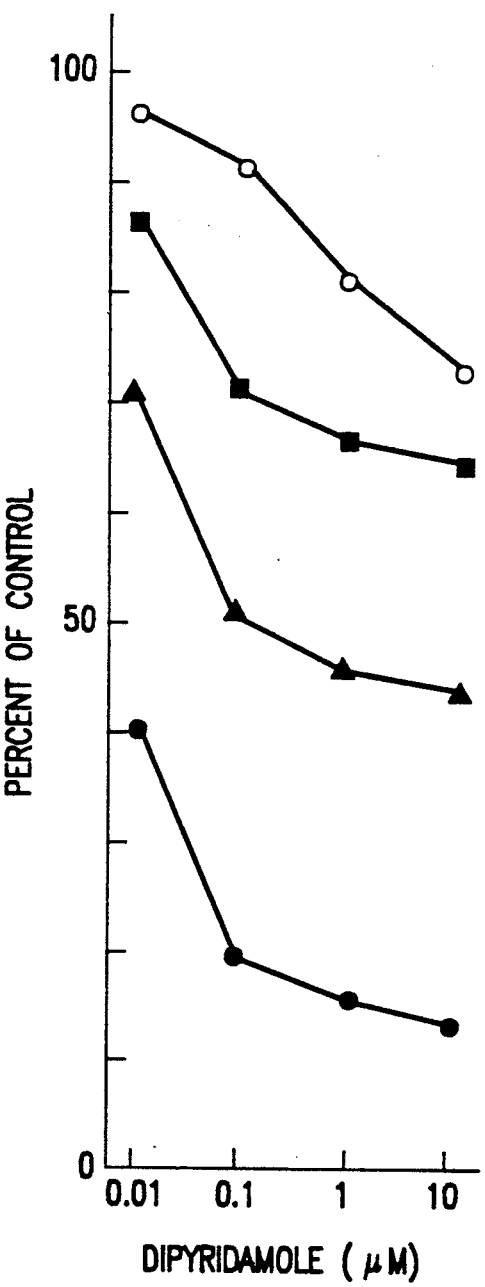
Figure 5B:
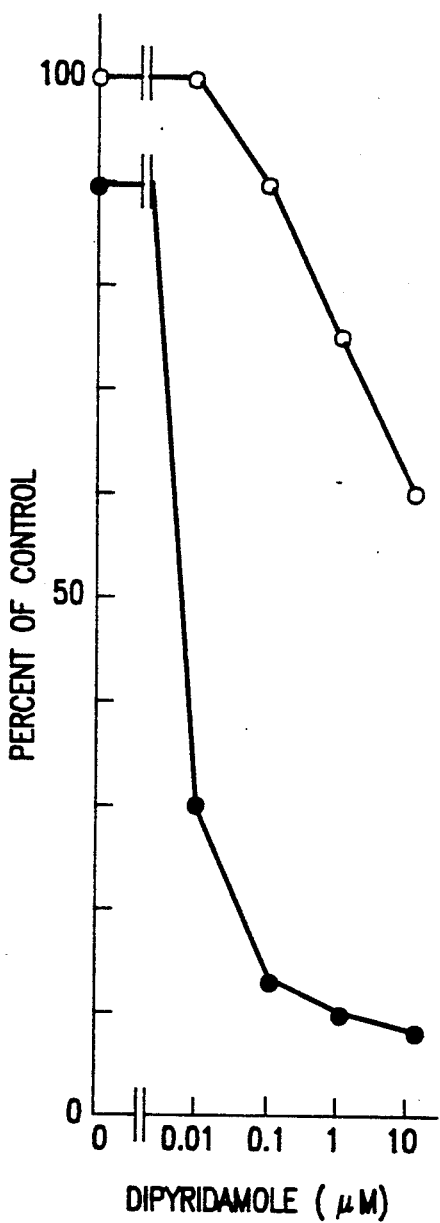
Figure 6A:
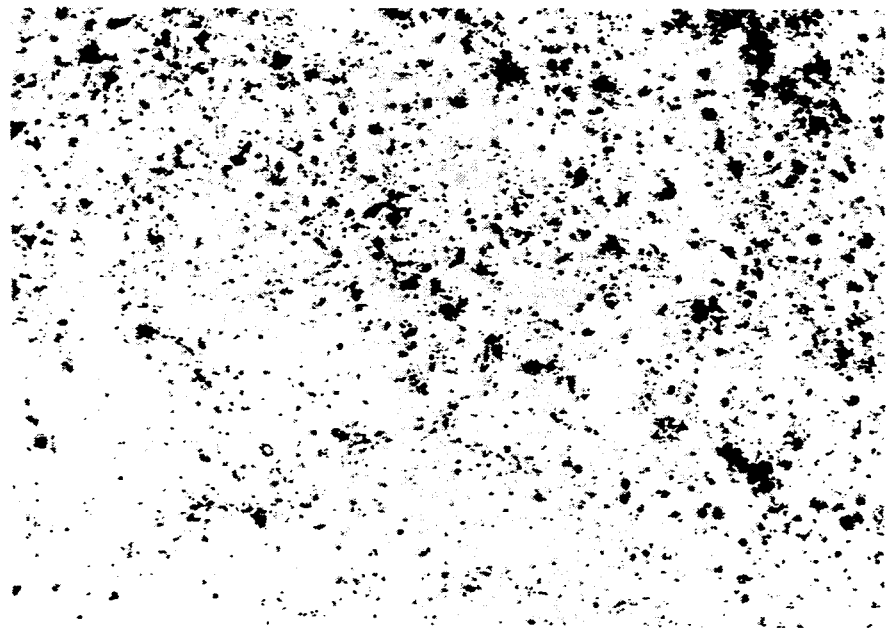
Figure 6B:
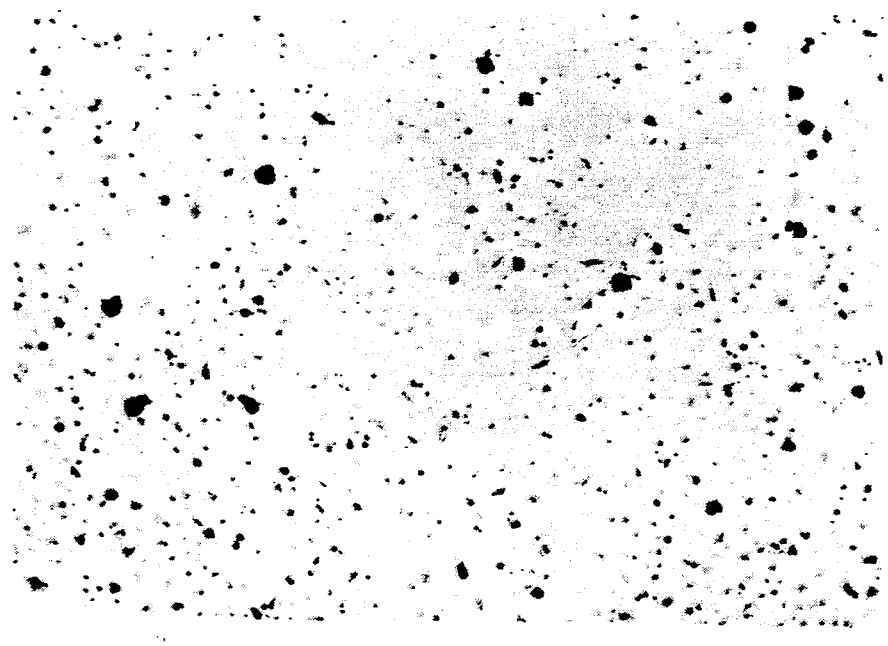
Figure 6C:
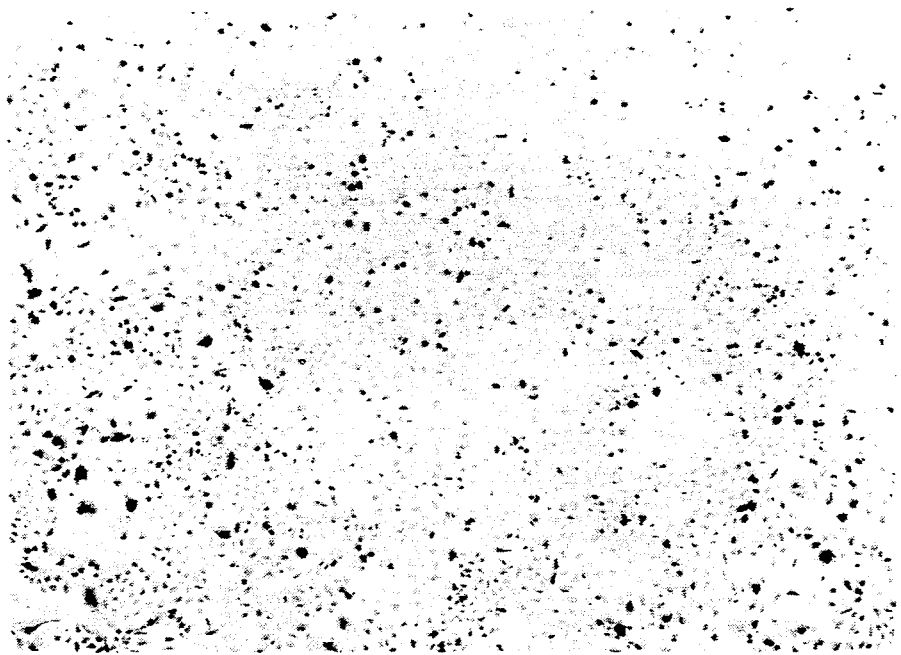
Figure 6D:
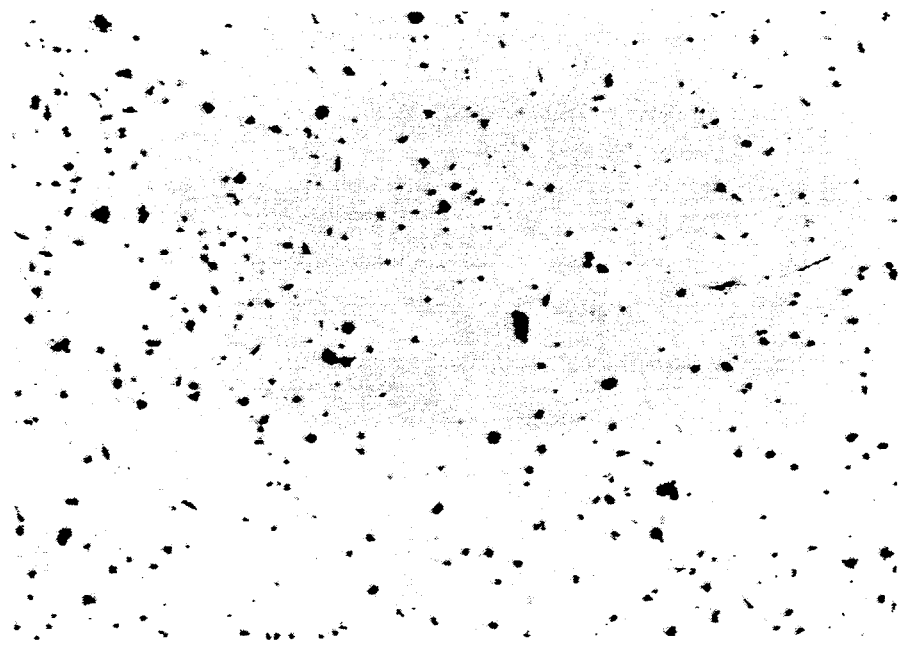
Figure 7A:
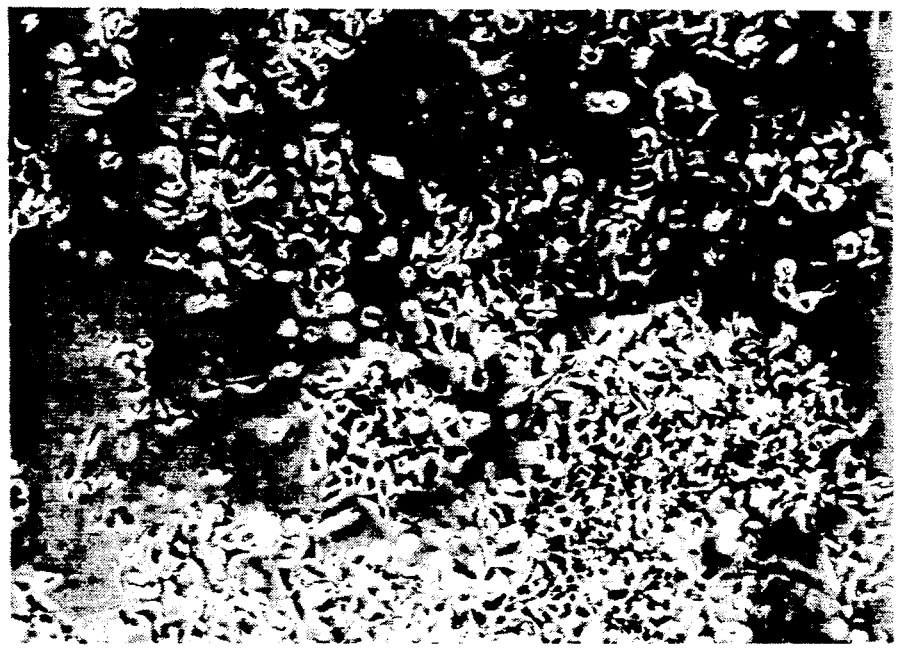
Figure 7B:
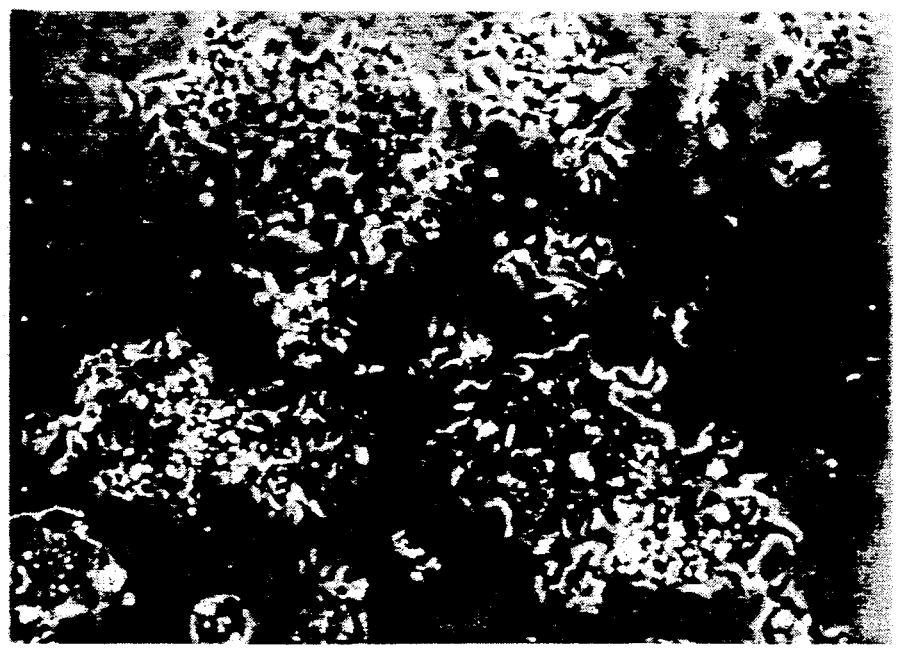
Figure 7C:
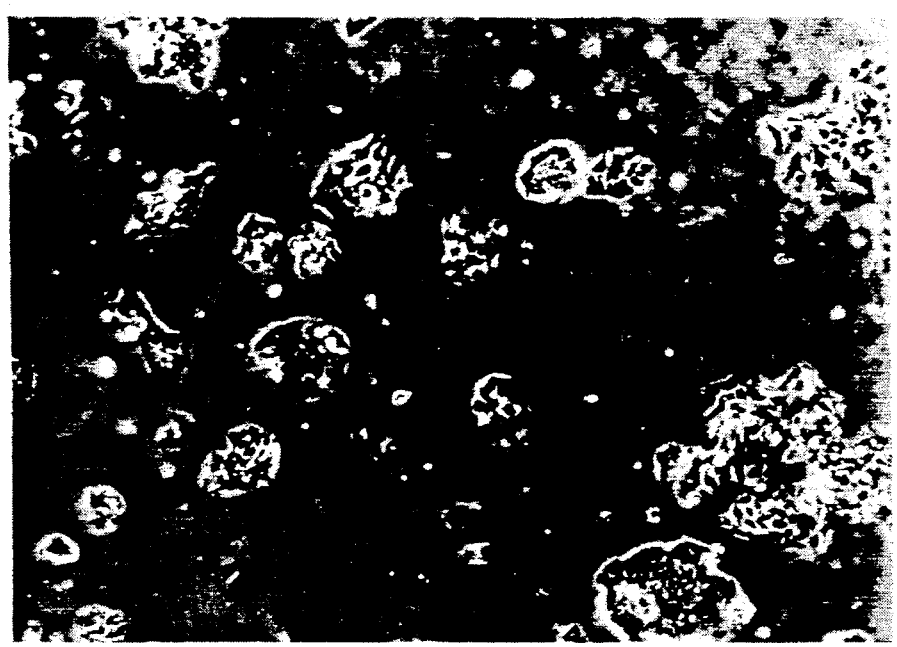
Figure 7D:

The concentration of dipyridamole in blood during the several hours after its administration is a few micromoles, whereas the present inventors found the most effective concentration for the synergistic enhancement of HuIFN action was much less, i.e., less than 0.1 $\mu$M (FIGS. 3B, 4B and 5B). Results in FIGS. 3A, 4B and 5B revealed that very low unit concentration of HuIFN (less than 10 units/ml) was also effective for the anticellular action even when applied in combination with low concentrations of dipyridamole. Therefore, dipyridamole may also enable a reduction in the dosage of HuIFN in the treatment of tumor.

IFN-susceptibility varies among different cell types (Strander et al., *Adv. Cancer Res.*, Academic Press, London, 46 (1986); Stewart II, *The Interferon System*, Springer-Verlag, Wien/New York (1981); Yarosh et al., *Carcinogenesis* 6:883–886 (1985)); but there exists positive correlation between the survival susceptibility and DNA-synthesis levels in the treated cells (Suzuki et al., *J. Gen. Virol.* 67:651–661 (1986)). Estimation of DNA-synthesis level is a useful method for evaluating IFN-susceptibility and, further, requires no more time than does the cell proliferation inhibition test used here. Therefore, the synergism found was also confirmed by the DNA-synthesis levels in KT and RSa, well known to be highly sensitive to HuIFN (Suzuki et al., *J. Gen. Virol.* 67:651–661 (1986)).

Figure 8:
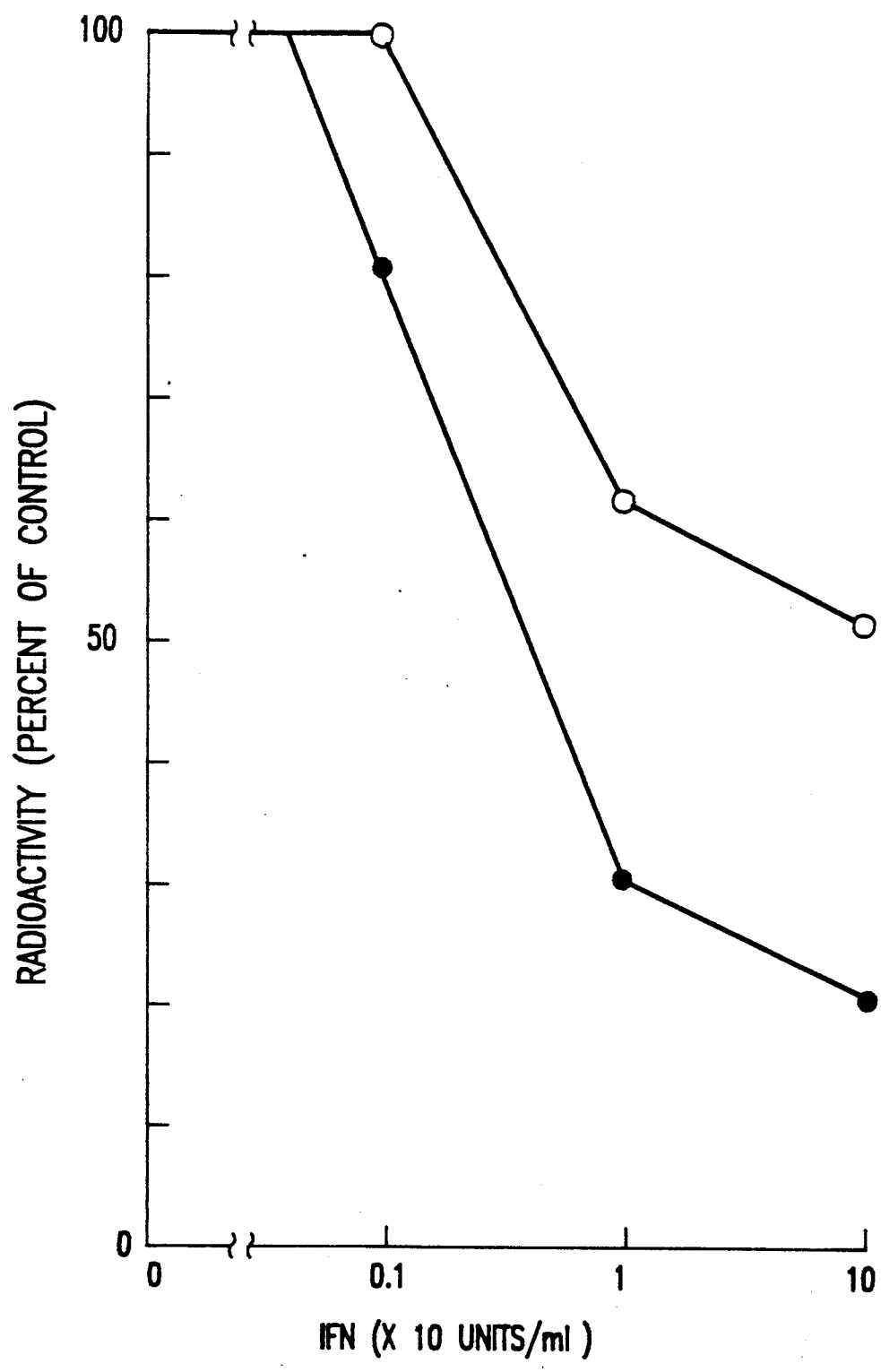

DNA synthesis in KT cells was inhibited by HuIFN-$\beta$ and its inhibitory effect was remarkably enhanced by 0.1 $\mu$M dipyridamole as shown in FIG. 8.

The results presented here are the first which show the surprising effect of dipyridamole on the anticellular action of HuIFN. As mentioned previously, a synergistic effect of mopidamole, a derivative of dipyridamole, on the antitumor effect of HuIFN has once been reported, but in further publications it was reported that no synergism was found. In a comparative study carried out by the present inventors, the DNA synthesis activity in RSa cells treated with 0.1 $\mu$M dipyridamole or mopidamole was inhibited less than with combined treatment with HuIFN-$\alpha$. When combined with 1 unit/ml HuIFN-$\alpha$ DNA synthesis was more strongly depressed as shown in Table 1. The combination dipyridamole/HuIFN-$\alpha$ was significantly more effective than mopidamole/HuIFN-$\alpha$.

TABLE 1

Comparison of inhibitors effect of DNA synthesis between dipyridamole and mopidamole (% of control)*

| Agents (0.1 $\mu$M) | HuIFN-$\alpha$ (unit/ml) | |
|---|---|---|
| | 0 | 1 |
| None | 100 | 91 |
| Dipyridamole | 92 | 61 |
| Mopidamole | 95 | 84 |

*Logarithmically-growing RSa cells were treated with agents or not for 24 hours, and then labelled with [$^3$H]dTHD, as described in J. Gen. Virol. 67:651–661 (1986).

The group of Galabov et al., as mentioned above, reported that dipyridamole induced IFN production. However, the present inventors found no detectable levels of antiviral activity in culture medium of 0.1 $\mu$M dipyridamole-treated cells in assay conditions described in *J. Gen. Virol.* 67:651–611 (1986).

As discussed above, addition of radiation or chemical anticancer agents to interferon therapy does not always augment their anticancer action, because interferon has the activity to enhance repair capacity, such as error-free DNA-repair of cellular damage caused by radiation and chemical anticancer agents. See Suzuki, N., et al., *Mutation Res.* 198:207–214 (1988), and Suzuki, N., et al., *Acta Biologica Hungarica*, in press. Therefore, it is important to understand what is the molecular mechanism of cell proliferation inhibition by interferon. This information can then be used to provide suppression of only cancer cell growth.

Figure 9:
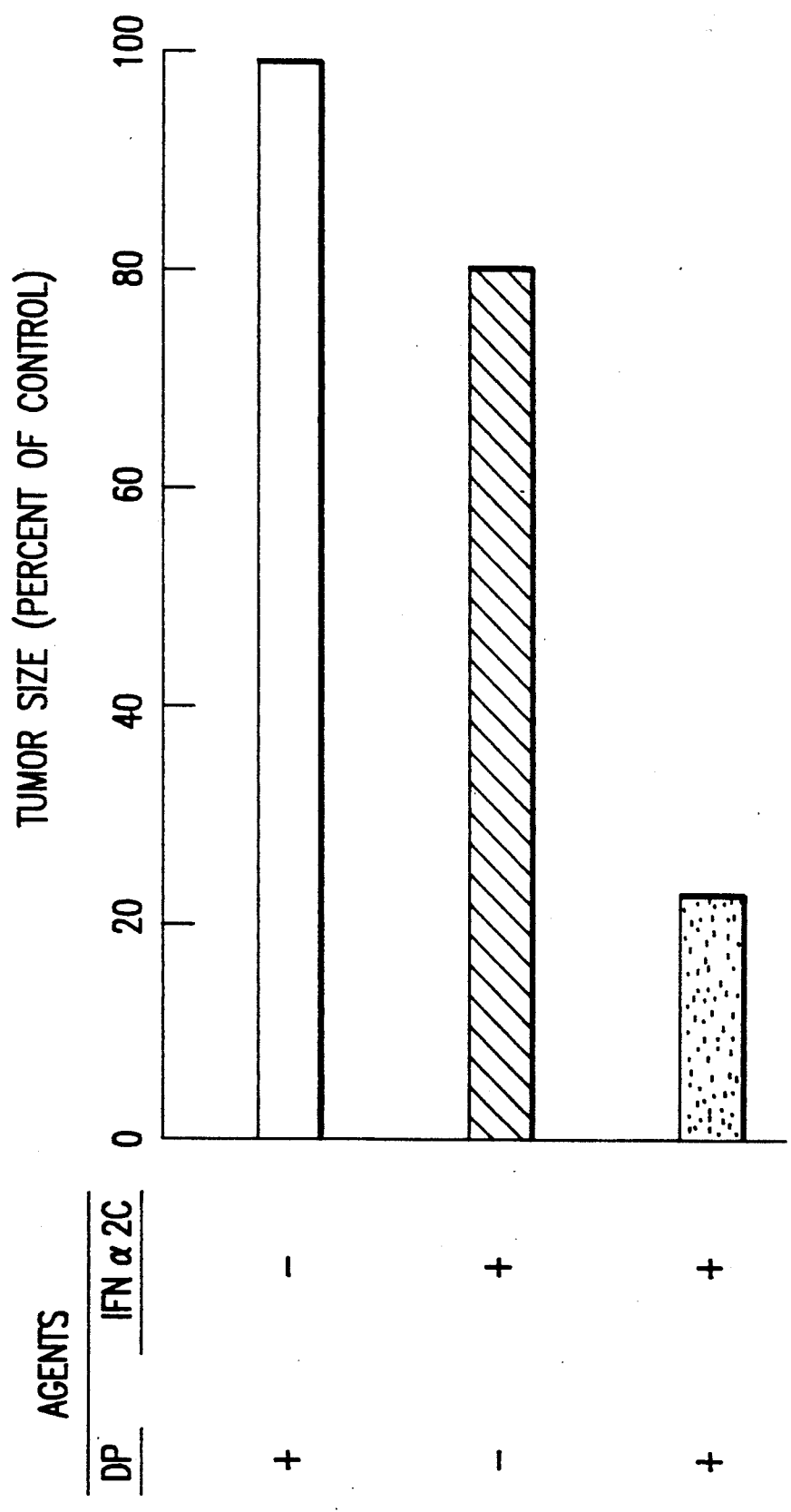

It was shown that tumor growth induced by injection of MM-1CB cells in nude mice was more noticeably inhibited by treatment with the combination of dipyridamole and interferon 3 days after the injection compared to treatment with each agent alone (FIG. 9). However, when the two agents were administered to nude mice after the tumor reached more than about 1 cm in diameter, the combination treatment was not drastically effective in depressing tumor growth (FIG. 10).

Figure 10:
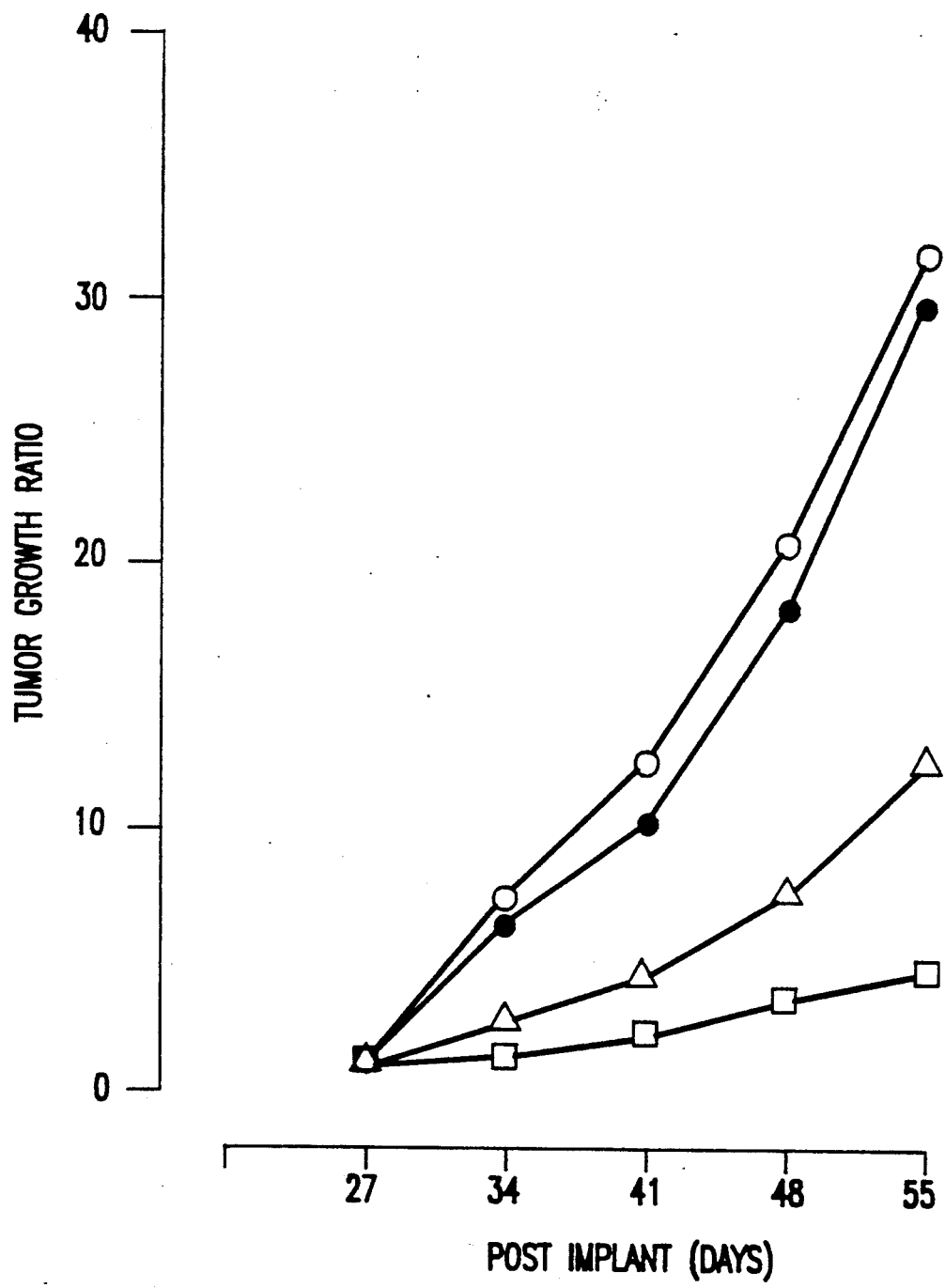
Figure 11:
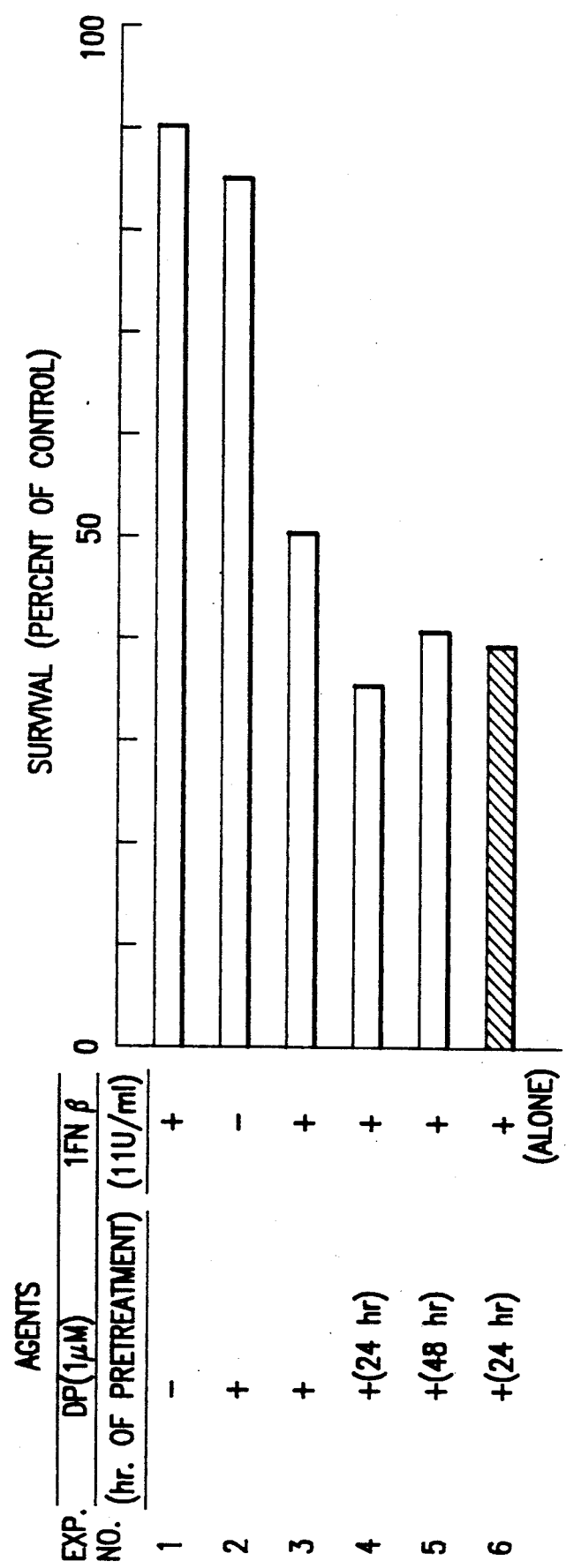
Figure 12B:
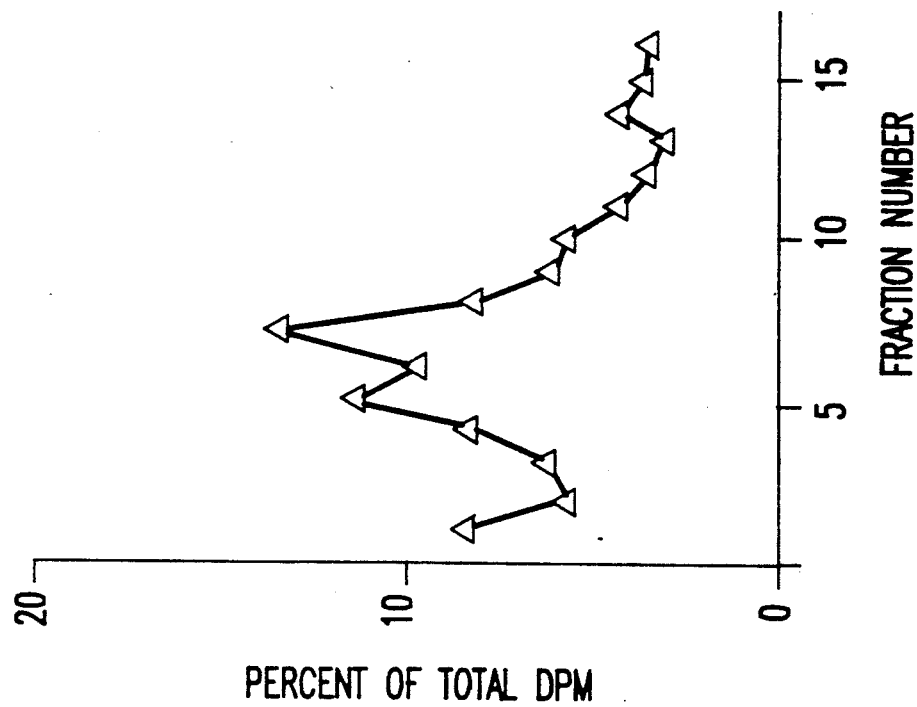
Figure 12A:
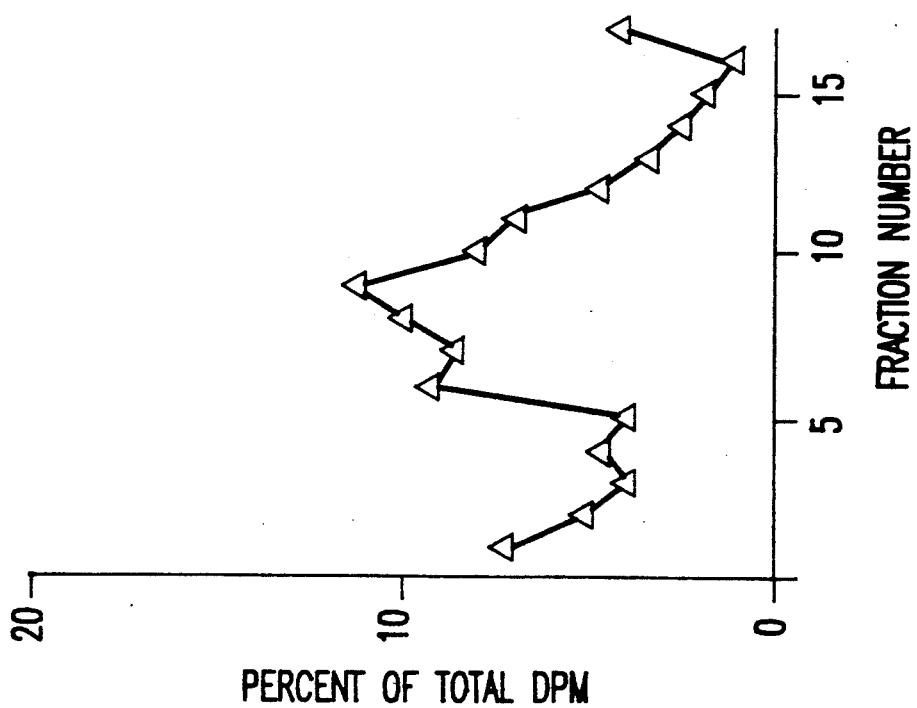
Figure 12D:
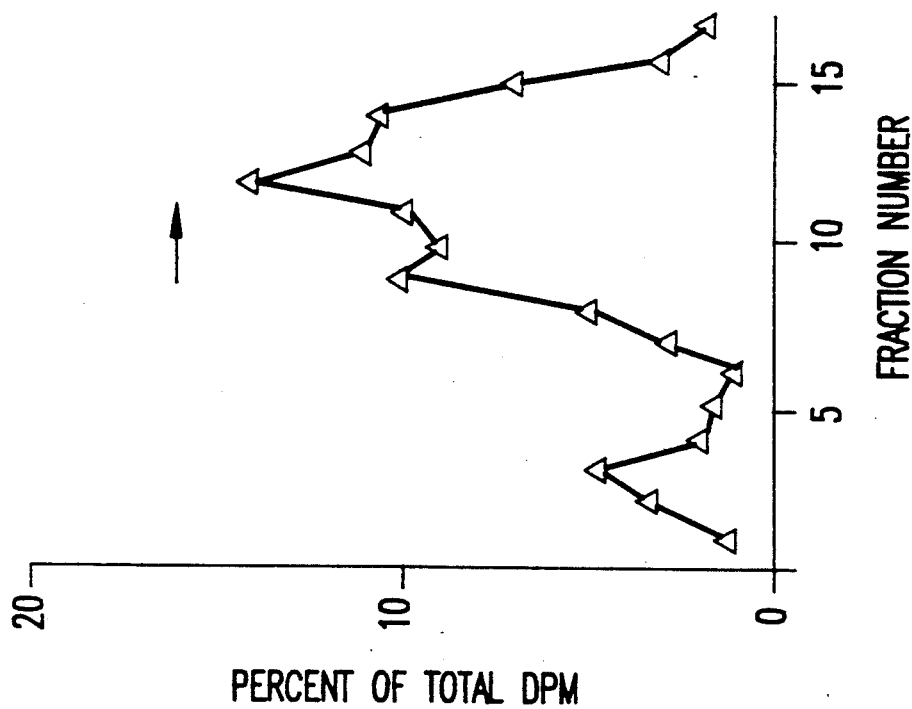
Figure 12C:
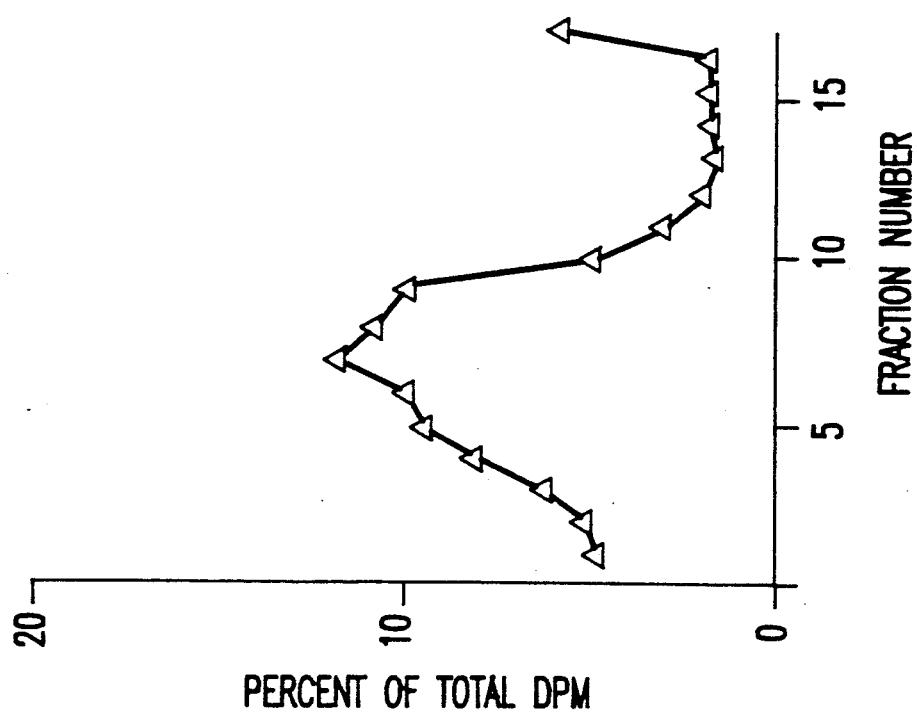

As demonstrated in FIG. 10, dipyridamole treatment prior to the addition of interferon was more effective than a simultaneous administration of the two agents. This enhanced effectiveness by pretreatment was found on both the growth of MM-1CB cells implanted in nude mice (FIG. 10) and on proliferation of the cells cultured in dishes (FIG. 11). Thus, the above results in vivo and in vitro demonstrate that dipyridamole alone enhances interferon activity.

The cross-sensitivity between interferon and ultraviolet rays and/or X rays, well-known DNA-damaging agents in human cell strains, has been reported (see Suzuki, N., et al., *Jpn. J. Cancer Res.* (Gann) 79:1184–1192 (1988)). Therefore, attempts were made to clarify the cellular response mechanism, after pretreatment with dipyridamole followed by interferon treatment, by focusing on DNA metabolism of the treated cancer cells. FIG. 12 demonstrates that pretreatment with dipyridamole followed by interferon-treatment alone resulted in damaged DNA, detected under alkaline assay conditions. This DNA damage may have enhanced the inhibitory action of interferon on cell proliferation. In fact, even interferon treatment alone after pretreatment with dipyridamole, depletion of the dipyridamole-containing medium and then washing of the cells, had a more marked inhibitory effect on MM-1CB cells than interferon-treatment alone without dipyridamole pretreatment (FIG. 11).

Figure 13:
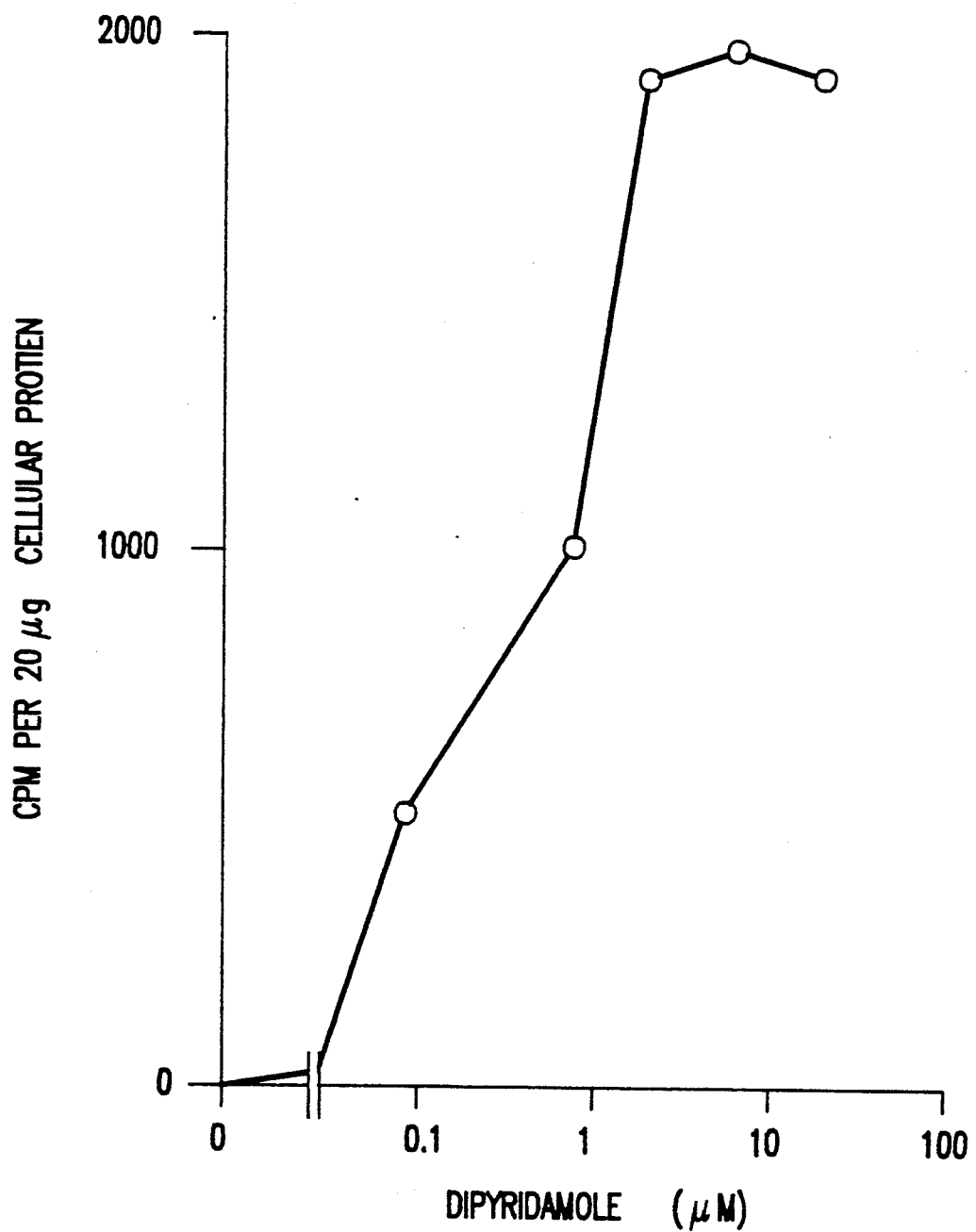

The cellular effects of dipyridamole alone was also examined and various effects other than those previously reported were found. Among the early responses after dipyridamole treatment, it is interesting to note that the activity of plasminogen activator-like protease was induced after a few minutes of treatment. The induction in MM-1CB cells 30 min after the treatment is shown in FIG. 13. The protease may be involved in various kinds of cellular function; for example, the induced protease might activate DNA-breakage activity of enzymes via proteolysis of their zymogen. The relationship between the protease induction by dipyridamole and DNA strand breakage combination with interferon are now being explored.

There have been no previous reports of DNA structure change by interferon or by dipyridamole. Furthermore, no relationship between the reported effects of dypyridamole, such as inhibition of nucleoside transport, and those of interferon have been reported. Therefore, the present findings (enhancement of interferon effects by dipyridamole via DNA structural change) represents the first such report.

Figure 14:
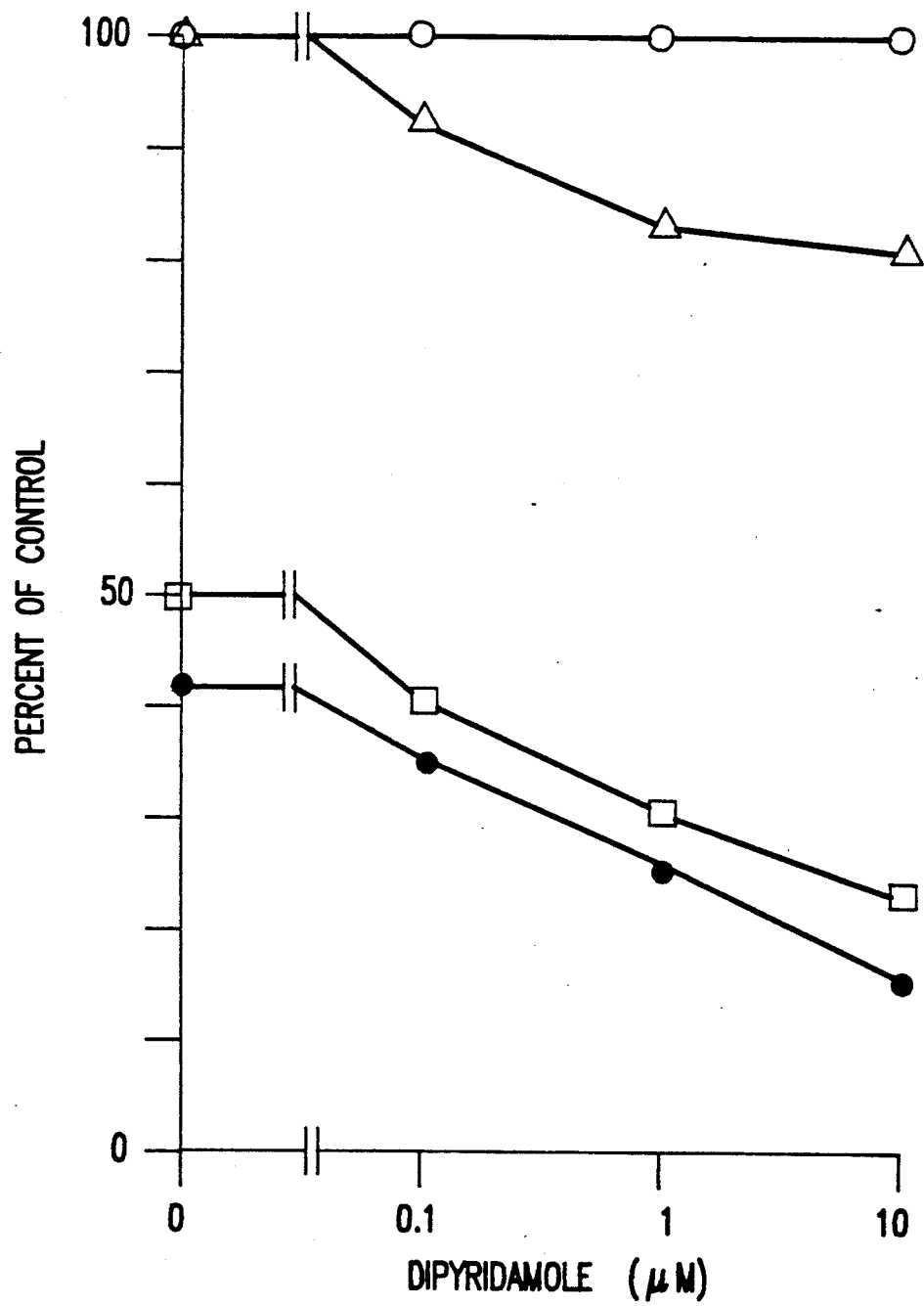

Any chemical agents used to modulate the action of interferon must do so without negative side-effects of the combined agents. Dipyridamole plus interferon is a suitable method for this purpose. Very low doses of dipyridamole (less than 1 $\mu$M) enhance the interferon effect in vitro. FIG. 14 presents further evidence that dipyridamole, with little inhibitory effect on cell proliferation, can enhance cell proliferation inhibition induced by interferon. The results also indicate that the present findings do not depend on reported cytocidal effects of dipyridamole.

While the reported results may point to DNA structural changes as the mechanism of action for the two agents, the synergistic effect reported and claimed herein is independent of a particular mechanism of action. Of importance is that dipyridamole enhances the antitumor action of interferon when administered simultaneously with or prior to the administration of intereferon.

The examples below are for illustrative purposes only and are not deemed to limit the scope of the invention.

EXAMPLE 1

| Lyophilized preparation containing 2 mg rHuIFN-$\gamma$ | |
|---|---|
| (1) rHuIFN-$\gamma$ | 2 mg/ml (2 × 10$^6$ I.U.) |
| (2) serum albumin (human) | 10.000 mg/ml |
| (3) NaCl | 1.750 mg/ml |
| (4) manintol | 40.000 mg/ml |
| (5) polyoxyethylene (20) sorbitanmonooleate | 0.300 mg/ml |
| (6) succinic acid | 2.36 mg/ml |
| (7) 1N NaOH | 36.26 mg/ml |
| (8) water for injection | 1.00 ml |

Preparation

The salts and other additives (2)–(7) are dissolved in ⅔ of the total required amount of water. The exact amount of HuIFN-$\gamma$ is then added and the solution is brought to the final required volume by adding the remaining water, filtered through 0.22 $\mu$M filter and filled into vials, lyophilized and stoppered.

EXAMPLE 2

| Lyophilized preparation containing 0.03 mg I.U. rHuIFN-$\alpha_{2c}$ | |
|---|---|
| (1) rHuIFN-$\alpha_{2c}$ | 0.03 mg (3 × 10$^6$ I.U.) |
| (2) isotonic phosphate buffer pH 7 | q.s. |
| (3) human serum albumin | 20.0 mg |
| (4) water for injection | 1.0 ml |

Preparation

Prepared analogously to Example 1.

EXAMPLE 3

| Lyophilized preparation containing 1 × 10$^6$ I.U. HuIFN-$\beta$ | |
|---|---|
| (1) rHuIFN-$\beta$ | 1 × 10$^6$ I.U. |
| (2) isotonic phosphate buffer pH7 | q.s. |
| (3) human serum albumin | 20.0 mg |
| (4) water for injection | 1.0 ml |

Preparation

Prepared analogously to Example 1.

EXAMPLE 4

| Lyophilized preparation containing 1 × 10$^6$–3 × 10$^6$ I.U. rHuIFN-$\alpha_2$ | |
|---|---|
| (1) IFN-$\alpha$2 | 1 × 10$^6$–3 × 10$^6$ I.U. |
| (2) KCl | 0.2 mg |
| (3) Na$_2$PHO$_4$.12H$_2$O | 2.88 mg |
| (4) KH$_2$PO$_4$ | 0.2 mg |
| (5) NaCl | 8.0 mg |
| (6) human serum albumin | 20.0 mg |
| (7) water for injection | 1.0 ml |

Preparation

The buffer materials (2), (3), (4), the stabilizer (6), the sodium chloride (5) and the active ingredient (1) were dissolved in the water (7). After sterile filtration, the solution was filled into vials under sterile conditions and freeze dried.

EXAMPLE 5

| Lyophilized preparation containing $1\text{-}3 \times 10^6$ I.U. rHuIFN-$\beta$ | |
| --- | --- |
| (1) IFN-$\beta$ | $1\text{-}3 \times 10^6$ I.U. |
| (2) KCl | 0.2 mg |
| (3) Na$_2$HPO$_4$.12H$_2$O | 2.88 mg |
| (4) KH$_2$PO$_4$ | 0.2 mg |
| (5) NaCl | 8.0 mg |
| (6) human serum albumin | 20.0 mg |
| (7) water for injection | 1.0 ml |

Preparation

Prepared analogously to Example 4.

EXAMPLE 6

| Lyophilized preparation containing $1 \times 10^6\text{-}3 \times 10^6$ I.U. rHuIFN-$\gamma$ | |
| --- | --- |
| (1) IFN-$\gamma$ | $1 \times 10^6\text{-}3 \times 10^6$ I.U. |
| (2) Na$_2$HPO$_4$.12H$_2$O | 2.31 mg |
| (3) NaH$_2$PO$_4$.2H$_2$O | 0.55 mg |
| (4) human serum albumin | 1.0 ml |

Preparation

Prepared analogously to Example 4.

EXAMPLE 7

| Dragee containing 30 mg dipyridamole | |
| --- | --- |
| Composition | |
| (1) Dipyridamole | 30.0 mg |
| (2) lactic acid | 30.0 mg |
| (3) potato starch | 17.5 mg |
| (4) aerosol | 1.5 mg |
| (5) magnesium stearate | 1.0 mg |

(1)+(2)+(3) were mixed and to the mixture was added water to form a moist mass.

The moist mass was passed through a sieve having 1.6 mm spacing and dried at 45° C. in a drying chamber. The dry granules were passed through a sieve having 1 mm spacing and mixed with (4) and (5).

The final mixture was pressed to form dragees.

Core weight 80 mg

The dragee cores formed were covered by a surface coating in known manner, the coating consisting essentially of sugar and talc. This coating may also contain permitted coloring agent. The finished dragees are polished with wax.

Dragee weight 120 mg

EXAMPLE 8

| Ampule containing 10 mg dipyridamole | |
| --- | --- |
| dipyridamole | 10 mg |
| tartaric acid | 4 mg |
| polyethylene glycol | 100 mg |
| hydrochloric acid (IN) to adjust to pH 2.7 | q.s. (~0.018 m) |
| water for injection add. | 2 ml |

The dipyridamole and other ingredients were dissolved in water. After sterile filtration, the solution is filled into ampules and sterilized by heating.

EXAMPLE 9

An ampule from Examples 1 to 6 is formulated for injection using water for injection or isotonic saline solution to provide an injection solution of 2 ml.

EXAMPLE 10

Combination preparation containing dipyridamole and HuIFN

The contents of the ampule from Examples to 6 were reconstituted with the contents of the dipyridamole ampule from Example 8.

The combination preparation of HuIFN$\alpha_2$ and HuIFN-$\beta$ with dipyridamole was stable at room temperature for about 6 hours. The HuIFN-$\gamma$/dipyridamole preparation should be used immediately after reconstitution of the lyophylisate.

EXAMPLE 11

Capsules containing delayed-release dipyridamole formations

30 Kg of rounded tartaric acid starter pellets is sprayed, in a special pan, with a suspension consisting of isopropanol, dipyridamole and polyvinylpyrrolidone until the resulting pellets of active substance contain about 45% dipyridamole.

These pellets are sprayed with a lacquer consisting of methacrylic acid/methyl methacrylate copolymer (brand name Eudragit S) and hydroxypropylmethylcellulose phthalate (brand name HP 55) in a weight ratio 85:15 to 50:50.

The organic lacquer solution also contains plasticizer and talc. Two pellet components are sprayed with 5% and 7% of coating and different ratios of lacquer components within the limits specified and are mixed together.

In a special capsule making machine, the quantity of pellets corresponding to 20-25 mg of dipyridamole are packed into an appropriate sized capsules.

We claim:

1. A method of treating tumors, said method comprising contacting said tumors with dipyridamole in a pretreatment step, followed by administration of interferon.

2. The method of claim 1, wherein said pretreatment step is followed by administration in combination with dipyridamole.

3. The method of claim 1, wherein said interferon is selected from the group of interferons consisting of:
   (a) $\alpha$-interferon;
   (b) $\beta$-interferon; and
   (c) $\gamma$-interferon.

4. The method of claim 1, wherein said interferon is administered parenterally.

5. The method of treating tumors of claim 1, wherein said dipyridamole is administered orally.

6. The method of treating tumors of claim 1, wherein said dipyridamole is administered parenterally.

7. The method of treating tumors of claim 1, wherein said dipyridamole is in an accelerated release form.

8. The method of claim 1, wherein said dipyridamole is in a delayed release form.

9. The method of claim 1, wherein said interferon has been reconstituted from a lyophilized form.

10. The method of claim 1, wherein said interferon is mixed with a pharmaceutically acceptable carrier substance.

11. The method of claim 1, wherein said dipyridamole is administered in dosages of 25–100 mg.

12. The method of claim 11, wherein said dipyridamole is administered in dosages of 30–60 mg twice daily.

13. A method for enhancing the tumor growth inhibitory action of an interferon, said method comprising: administering dipyridamole to a patient, or a pharmaceutically acceptable salt thereof, in a pretreatment step followed by administration of interferon to the patient, wherein said dipyridamole is in an amount sufficient to enhance the inhibitory action of said interferon.

14. The method of claim 13, wherein said pretreatment step is followed by administration in combination with dipyridamole.

15. The method of claim 13, wherein said interferon is selected from the group of interferons consisting of:
   (a) α-interferon;
   (b) β-interferon; and
   (c) γ-interferon.

16. The method of claim 13, wherein said dipyridamole is administered in dosages of 25–100 mg twice daily.

17. The method of claim 13, wherein said dipyridamole is administered in dosages of 30–60 mg twice daily.